United States Patent [19]

Cummins et al.

[11] Patent Number: 5,596,408
[45] Date of Patent: Jan. 21, 1997

[54] TURBIDITY SENSOR WITH REPLACEABLE COVERS

[75] Inventors: Brad L. Cummins, Freeport; Timothy K. Erickson, Lena; Gary R. O'Brien, Freeport; Alan V. Sheriff, Freeport; Duane J. Sies, Freeport, all of Ill.

[73] Assignee: Honeywell Inc., Minneapolis, Minn.

[21] Appl. No.: 646,217

[22] Filed: May 7, 1996

[51] Int. Cl.$^6$ ............................................. G01N 21/00
[52] U.S. Cl. ..................... 356/339; 356/440; 68/12.27
[58] Field of Search ............................. 356/343, 340, 356/338, 339, 440, 441, 442; 68/12.27, 12.02

[56] References Cited

U.S. PATENT DOCUMENTS

| | | | |
|---|---|---|---|
| 5,291,626 | 3/1994 | Molnar et al. | 356/339 |
| 5,446,531 | 8/1995 | Boyer et al. | 356/72 |
| 5,485,013 | 1/1996 | Cummins | 356/343 |

Primary Examiner—Frank Gonzalez
Assistant Examiner—Amanda Merlino
Attorney, Agent, or Firm—William D. Lanyi

[57] ABSTRACT

A turbidity sensor is provided in which a light source, a first photosensitive device and a second photosensitive device are arranged in a manner that permits easy removal and replacement of a cover which is used to protect the components. The cover is attachable to a support structure. The light source, which can be a light emitting diode, is attached to the support structure. The first and second photosensitive devices are also attached to the support structure. Light scattered by particulates in a fluid are directed toward the support structure and received by the second photosensitive device. Light which passes through a detection zone and is not scattered by the particular matter in the monitored fluid passes to a first photosensitive device. Many different types and shapes of covers can be used in conjunction with a single style support structure. This flexibility simplifies the manufacture of the turbidity sensors and reduces the costs that would otherwise be incurred if individual support structures were necessary for each different style of cover.

15 Claims, 9 Drawing Sheets

TURBIDITY SENSOR WITH REPLACEABLE COVERS

BACKGROUND OF THE INVENTION

1. Field of the Invention

The present invention is generally related to turbidity sensors and, more particularly, to a turbidity sensor that arranges a light source and two photosensitive devices in such a way as to permit easy removal and replacement of transparent covers with respect to the circuitry and components of the sensor wherein the covers, are attachable to a support structure.

2. Description of the Prior Art

Various types of turbidity sensors are known to those skilled in the art. Turbidity sensors have been used in appliances, such as dishwashers, to monitor the turbidity of the wash fluid during the washing process. U.S. Pat. No. 5,446,531, which issued to Boyer et al on Aug. 29, 1995, describes a sensor platform for use in machines for washing articles. A plurality of fluid condition sensors are combined together to provide a sensor cluster that senses turbidity, temperature, conductivity and the movement of a ferromagnetic object. The plurality of sensors are attached to a substrate and encapsulated, by an overmolding process, with a light transmissive and fluid impermeable material. The sensor cluster can be disposed at numerous different locations within a body of fluid and does not require a conduit to direct the fluid to a particular location proximate the sensor. In a preferred embodiment of invention, a circuit is provided which monitors the signal strength of first and second light sensitive components to determine turbidity and, in addition, those signals strengths are also used to advantageously determine the most efficient magnitude of current necessary to drive a light source, such as a light emitting diode. By controlling the current to a light emitting diode as a function of the strength of light signal received by first and second light sensitive components, the turbidity sensor can be operated at a more efficient and effective level.

U.S. Pat. No. 5,444,531, which issued to Foreman et al on Aug. 22, 1995, discloses a sensor with LED current control for use in machines for washing articles. Similar to the basic structure of the turbidity sensor described in U.S. Pat. No. 5,446,531, this turbidity sensor controls the current flowing through a light emitting diode in response to signals received from two photosensitive components.

U.S. Pat. No. 5,485,013, which issued to Cummins on Jan. 16, 1996, discloses a turbidity sensor with a light aperture arrangement of two openings formed in two parallel plates. The turbidity sensor is provided with two plates which each have an aperture formed therethrough. The apertures are aligned to define a light passage from a light source such as a light emitting diode. By properly selecting the gap between the two plates and the size of the two apertures, the angle of divergence of light emanating from the light source can be controlled and reduced to a magnitude that prevents light from passing directly from the light source to a scattered light detector of the turbidity sensor. The arrangement avoids the necessity of using expensive focusing lens.

U.S. Pat. No. 5,291,626, which issued to Molnar et al on Mar. 8, 1994, discloses a machine for cleansing articles, such as a dishwasher. The machine incorporates a device for measuring the turbidity of at least partially transparent liquid. The device includes a sensor for detecting scattered electromagnetic radiation, regardless of polarization, and a sense for detecting transmitted electromagnetic radiation, regardless of polarization.

SUMMARY OF THE INVENTION

A turbidity sensor made in accordance with the present invention comprises a support structure. A light source is attached to the support structure. A first photosensitive device is attached to the support structure and aligned with the light source so that the light source transmits a beam of light to the first photosensitive device in a direction along a first path line. The first path line is disposed within a first plane which intersects the support structure. The first path line is also disposed within a second plane which is in nonintersecting relation with the support structure. The first plane is perpendicular to the second plane. The present invention further comprises a second photosensitive device that is attached to the support structure and aligned to receive light from the light source which is scattered in a direction along a second path line by a fluid within a detection zone. The second path line is disposed within the first plane and is perpendicular to the second plane. The detection zone is intersected by the first and second path lines and the first and second planes. A cover is attached to the support structure. The cover is provided with light transmissive portions in order to permit light to pass through the cover along the first and second path lines.

In a preferred embodiment of the present invention, the cover is shaped to conduct the fluid through the detection zone. The cover can also comprise a portion of a pump housing for a dishwasher. In certain embodiments of the present invention, the sensor is disposed within a dishwasher. The light source can be a light emitting diode and the first and second photosensitive devices can be photodiodes. In many applications of the present invention, the cover and the support structure are separable from each other in a direction perpendicular to the second plane.

BRIEF DESCRIPTION OF THE DRAWINGS

The present invention will be more fully and completely understood from a reading of the Description of the Preferred Embodiment in conjunction with the drawings, in which.

DESCRIPTION OF THE PREFERRED EMBODIMENT

Figure 1:
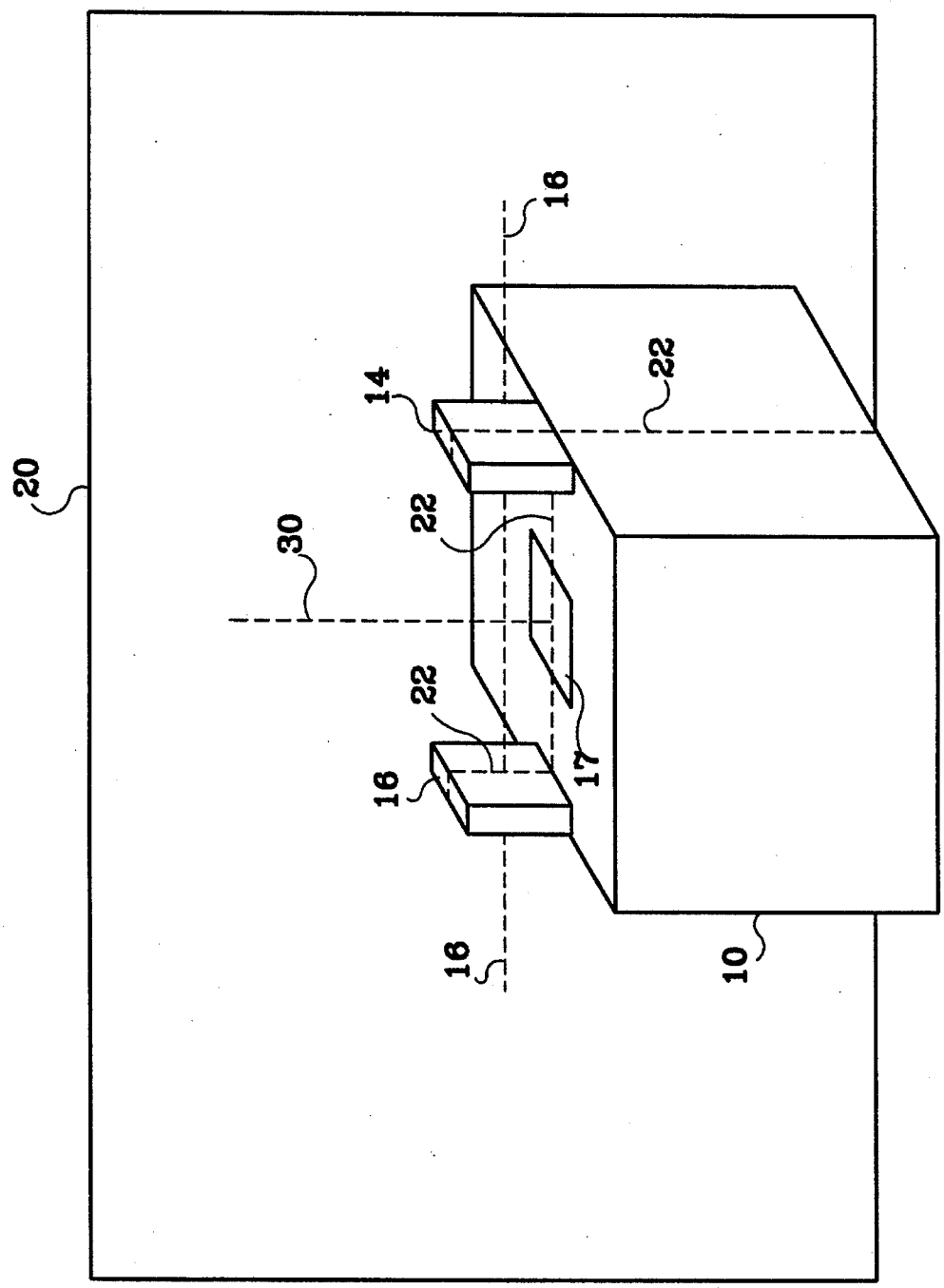
FIGS. 1 and 2 are schematic representations of the present invention used to show the geometric positions of various components.

Throughout the Description of the Preferred Embodiment, like components will be identified by like reference numerals.

It should be understood that the purpose of the present invention is to provide a turbidity sensor that permits easy replacement of its cover so that many different types of fluid conduits and fluid directing structures can be incorporated in combination with a basic support structure. In order to clearly describe the structure and operation of the present invention, it is necessary to describe the physical geometry of the components and explain various terms that will be used throughout this description. In FIG. 1, a support structure 10 is represented schematically by a generally rectangular box. The support structure 10, as will be described in greater detail below, typically comprises a printed circuit board and various electronic components used to control the operation of the turbidity sensor. However, in order to more clearly describe the important geometric terminology used in the discussion below, the support structure 10 is shown in a simplified and schematic representation. A light source 12 is attached to the support structure. In a typical application of the present invention, the light source 12 comprises a light emitting diode. A first photosensitive device 14 is also attached to the support structure 10. The first photosensitive device 14 is aligned with the light source 12 in such a way that light can pass from the light source 12 to the first photosensitive device 14 along a first path line 16. As can be seen in FIG. 1, the path line 16 extends between the light source 12 and the first photosensitive device 14.

With continued reference to FIG. 1, a first plane 20 is shown intersecting the support structure 10, the light source 12 and the first photosensitive device 14. It should be understood that the first plane 20 is an imaginary plane used for purposes of describing the structure of the present invention. The dashed lines identified by reference numeral 22 represent the intersection between the first plane 20 and the structure that comprises the support structure 10, the light source 12 and the first photosensitive device 14.

A second photosensitive device 17 is disposed as shown and aligned so that it can receive light transmitted by the light source 12 and scattered by a fluid disposed within a detection zone. The detection zone, which will be described in greater detail below, is located between the light source 12 and the first photosensitive device 14. The detection zone is also above the second photosensitive device 17 in FIG. 1. The detection zone is intersected by the first path line 16 and a second path line 30. The purpose of FIG. 1 is to illustrate the relative positions of the components of the turbidity sensor with respect to the first plane 20. Path lines 16 and 30 are disposed within the first plane 20.

Figure 2:
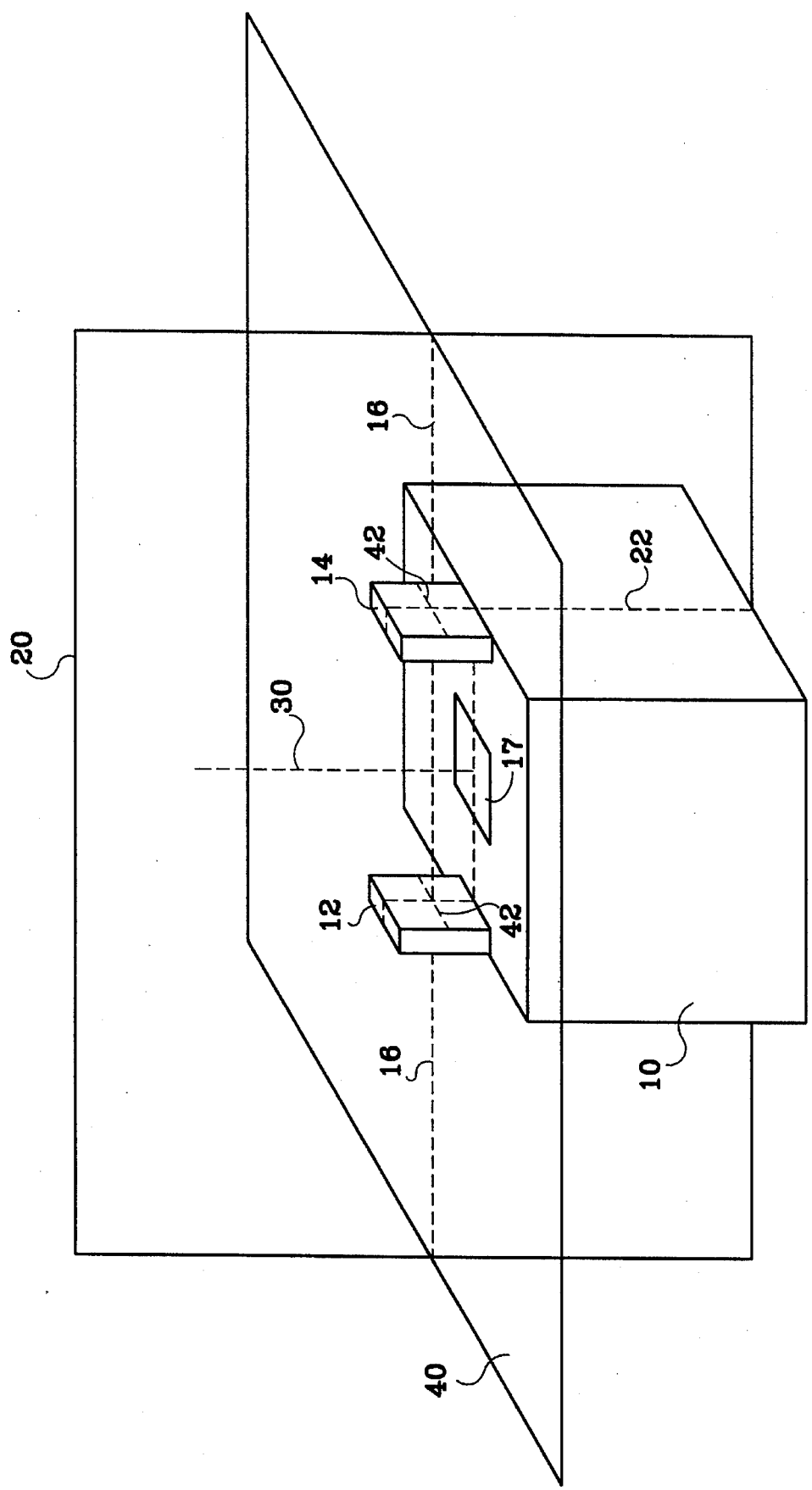

FIG. 2 is generally similar to FIG. 1, but with the addition of a second plane 40 that is disposed in nonintersecting relation with the support structure 10. The second plane 40 extends through the light source 12 and the first photosensitive device 14 and, as shown in FIG. 2, the first path line 16 is disposed within the second plane 40. The first path line 16 is also disposed within the first plane 20 and is located at the intersection of the first and second planes. The second path line 30 extends perpendicular to the second plane 40. It is important to note that the second path line 30, which represents the path along which scattered light will pass from the detection zone to the second photosensitive device 14, is perpendicular to the second plane 40 and, whereas the first path line 16 is disposed in both the first and second planes, the second path line 30 is disposed only in the first plane 20. Lines 42 show the intersection between the second plane 40 with the light source 12 and first photosensitive device 14. The geometric arrangement shown in FIG. 2 distinguishes the present invention from other known turbidity sensors in that the first and second path lines, 16 and 30, are not disposed within a common plane which is in nonintersecting relation with the support structure 10 of the turbidity sensor. The advantage of the arrangement shown in FIG. 2 is that it permits a much easier adaptation of replaceable covers and support structures 10 in the ways that will be described in greater detail below.

Throughout the Description of the Preferred Embodiment of the present invention, the covers and support structures will be described in terms of the cover being removable from the support structure and replaceable with a different cover. However, it should be clearly understood that one advantage of the present invention is that it allows a common cover to be used in conjunction with many different support structures 10. In other words, for a standard cover design, the support structure 10 may comprise two photosensitive components or one. In addition, the light emitting diode can be one that emits visible light or infrared light. Many other specific characteristics of the sensor can be implemented by changing the circuitry or software contained within the support structure 10. Therefore, it should be clearly understood that the separability of the cover and the support structure permit a high degree of flexibility, regardless of a single support structure is used with a plurality of removable covers or, conversely, if a single cover is used with a plurality of replaceable support structures.

Figure 3:
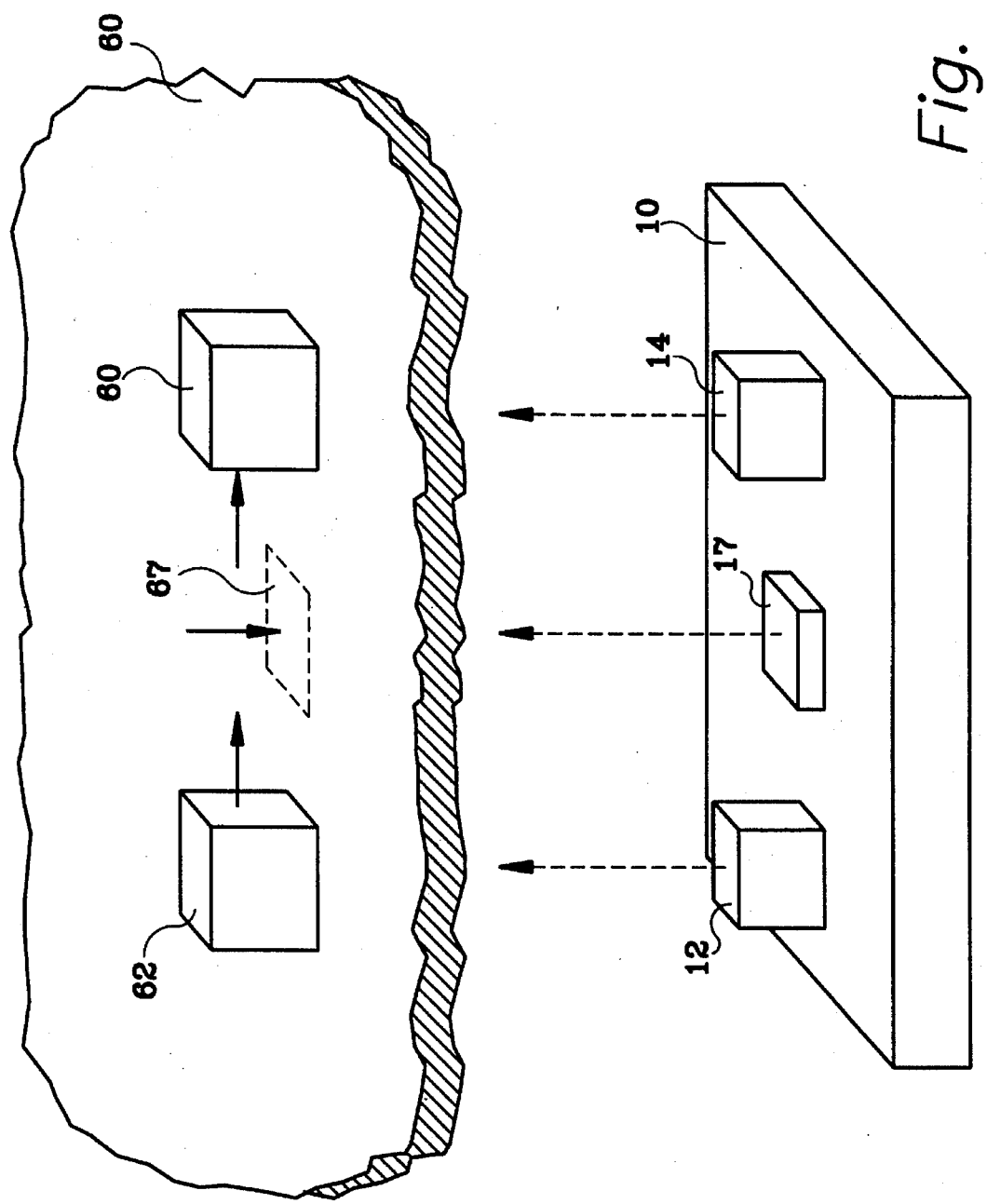
FIG. 3 shows one embodiment of the present invention.

FIG. 3 shows one embodiment of the present invention that is made possible by the geometric configuration described above in conjunction with FIGS. 1 and 2. If a cover 60 is shaped as shown in FIG. 3, with two raised hollow containments, 62 and 64, the support structure 10 can be moved upward in FIG. 3 to dispose the light source 12 within containment 62, the first photosensitive device 14 within containment 64 and the second photosensitive device 17 aligned with a transparent portion 67 of the cover 60. For example, the cover 60 in this embodiment can be a bottom portion of a pump housing used within a dishwasher. The support structure 10 would be moved, in the direction represented by the dashed line arrows in FIG. 3 to disposed the light source 12 and the first and second photosensitive devices, 14 and 17, in a position relative to the cover 60 so that the light source 12 can transmit a beam of light in the directions represented by the solid arrows in FIG. 3. The light would pass from the light source 12 through a transparent portion of containment 62 toward a detection zone directly above the transparent portion 67. Light that passes through the detection zone would continue to pass through a transparent portion of containment 64 and be received by the first photosensitive device 14. Light that is scattered by particulates within the detection zone would be scattered downward through the transparent portion 67 and be received by the second photosensitive device 17. It should be understood that the horizontal solid arrows in FIG. 3 are aligned with the first path line 16 and the vertical solid arrow above the transparent portion 67 is aligned with the second path line 30 in FIGS. 1 and 2. In FIG. 3, the cover 60 and the support structure 10 are shown schematically without any detail illustrating the means for attaching the support structure 10 to the cover 60 which, as discussed above, can be the bottom portion of a dishwasher pump housing. It should be understood that the support structure 10 could be provided with snap acting attachment members, as will be described in greater detail below in conjunction with FIG. 6, or it can be attached by conventional means such as screws. One advantage of the present invention is that a single pump housing can be used in conjunction with many different types of support structures and related electronic circuitry.

Depending on the particular model of dishwasher, highly complex turbidity sensors or extremely basic and simple turbidity sensors can be used in association with the same pump housing used as a cover for the sensor.

Figure 4:
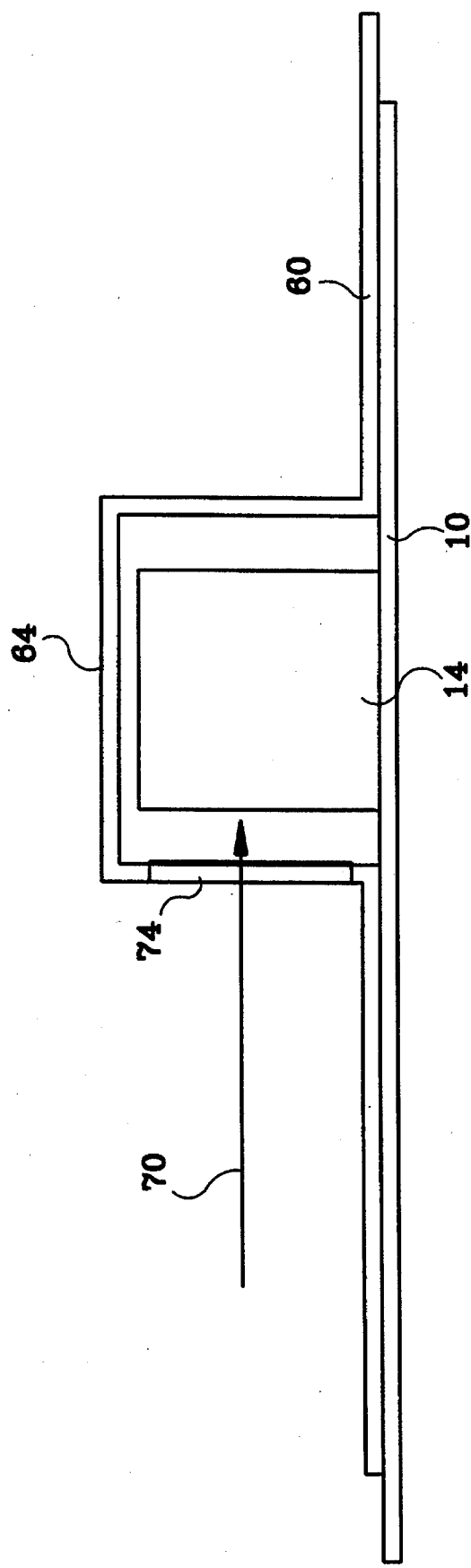
FIGS. 4 and 5 are sectional views of the illustration shown in FIG. 3.

FIG. 4 is an enlarged view of a portion of the device shown in FIG. 3. The first photosensitive device 14 is disposed within the hollow containment 64 that is formed as part of the cover 60. The first photosensitive device 14 is attached to the support structure 10, which is illustrated in the form of a printed circuit board in FIG. 4. Light passing directly from the light source, in the direction of arrow 70, passes through a transparent portion 74 of the containment 64. The containment 64, in combination with the cover 60, protects the first photosensitive device 14 and other associated circuit components from possible damage that could occur if these components were placed in direct contact with the fluid whose turbidity is being monitored. It should be understood that the entire cover 60 can be transparent.

Figure 5:
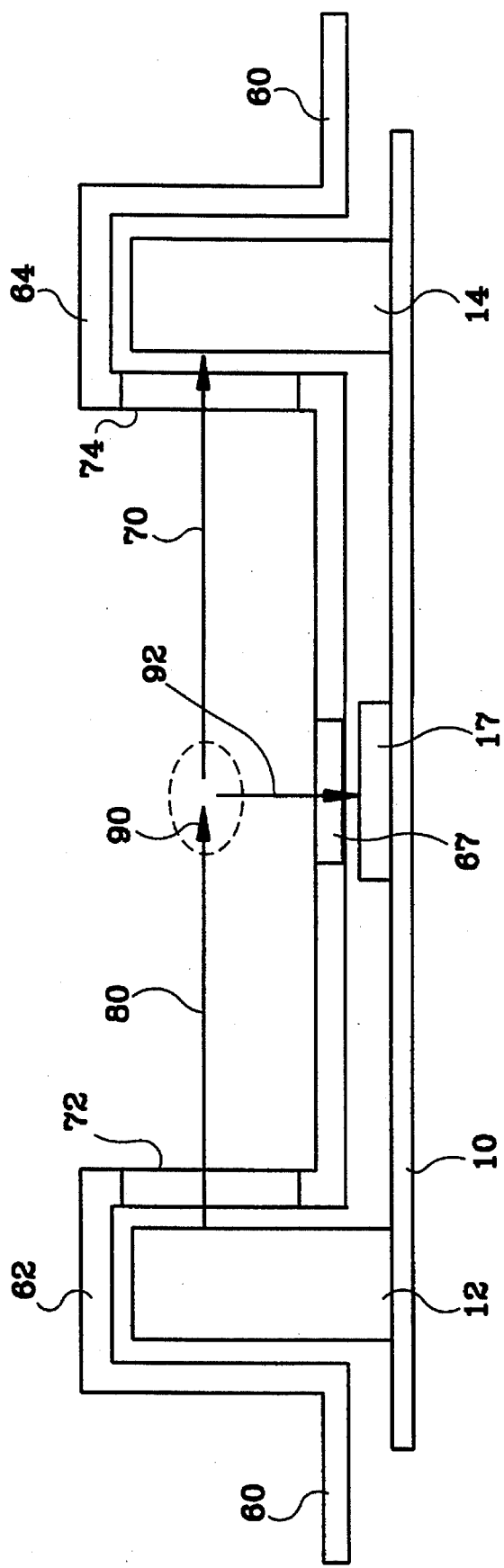

FIG. 5 is an alternative sectioned view of the device described above in conjunction with FIG. 3. The light source 12 is disposed within containment 62 and passes light, in the direction represented by arrow 80, through a transparent portion 72 toward the detection zone 90. The detection zone 90 is represented by a dashed elliptical shape in FIG. 5. However, it should be understood that the detection zone actually represents a much larger region disposed between the light source 10 and the first photosensitive device 14. When light passes through the detection zone, it is partially scattered by certain particulates within the fluid being monitored. Some of the light passes through the detection zone, as represented by arrow 70, and is received by the first photosensitive device 14. Other light is reflected by the particulates in the fluid and passes in a direction represented by arrow 92 toward the second photosensitive device 17. A transparent region 67 allows the light to pass through the cover 60 and be received by the second photosensitive device 17. Since the basic operation of a turbidity sensor is known to those skilled in the art and described in detail in the United States patents discussed above, the operation of the turbidity sensor will not be described in detail herein. The present invention more specifically related to the positions of the various components of the turbidity sensor and the arrangement of the support structure in combination with a cover that is removable and replaceable. As described above, the entire cover can be transparent.

FIG. 5 illustrates one of the most important advantages of the present invention. The second photosensitive device 17 is intended to receive light that is scattered by particulate matter within the detection zone 90. Because the second photosensitive device 17 is placed at its location to receive light that passes in the direction of arrow 92, it is much closer to the detection zone 92 than the first photosensitive device 14. The light path represented by arrows 70 and 80 can be very close to the surface of the cover, placing the detection zone 90 very close to the second photosensitive device 17. In certain applications, the close proximity of the second photosensitive device 17 to the detection zone 90 increases its sensitivity significantly. Since the intensity of light reflected by the particulate matter in the fluid being monitored may have a relatively low intensity compared to the transmitted light received by the first photosensitive device 14, this close proximity of the second photosensitive device 17 to the detection zone 90 is significantly advantageous. The intensity of light decreases as a squared function of the distance between the detection zone 90 and the second photosensitive device 17. Therefore, since the present invention allows the closer proximity of the detection zone 90 to the second photosensitive device 17, the sensitivity of the sensor with regard to the receipt of scattered light from the detection zone 90 is greatly enhanced. This is also very important if the light emitting diode emits infrared light and the photosensitive devices are sensitive to infrared light. The present invention facilitates the operation of a turbidity sensor with infrared components because of the close proximity provided between the detection zone 90 and the second photosensitive device 17.

Figure 6:
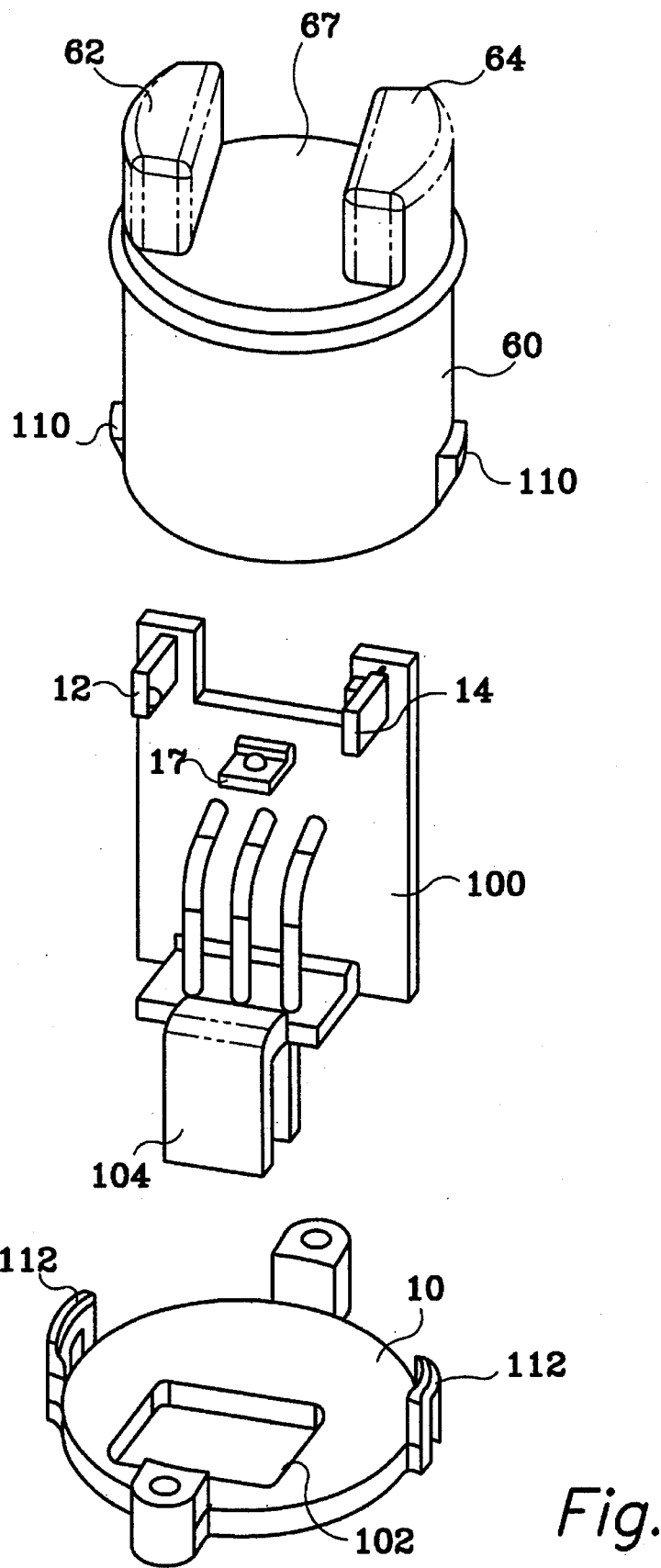
FIGS. 6 is an exploded view of a preferred embodiment of the present invention.

FIG. 6 shows one particularly preferred embodiment of the present invention. The support structure 10 is shaped to receive a printed circuit board 100 that can be attached thereto or, alternatively, captivated between the support structure 10 and the cover 60. The support structure 10 has an opening 102 which permits certain electrical connections 104 to extend downward through the opening 102. Although not shown in FIG. 6, the printed circuit board 100 can support various components that are used in conjunction with the light source 12 and the first and second photosensitive devices, 14 and 17. When the printed circuit board 100 is fastened to the support structure 10, the support structure 10 is effectively combined with the light source 12 and the photosensitive devices, 14 and 17, with the central structure in FIG. 6 held in place between the support structure 10 and the cover 60. The cover 60 can be attached to the support structure 10 through the use of protrusions 110 and fasteners 112. When the cover 60 is attached to the support structure 10 in this way, the light source 12 is disposed within the hollow containment 62 and the first photosensitive device 14 is disposed within the hollow containment 64. Both hollow containments, 62 and 64, are formed as part of the cover 60. Reference numeral 67 in FIG. 6 identifies the transparent portion 67 of the cover 60 that permits light to pass through it and be received by the second photosensitive device 17. The detection zone is located between the two containments, 62 and 64, that extend upward from the cover 60. As can be seen in FIG. 6, one significant advantage of the locations of the light source and photosensitive devices is that the cover 60, or vice versa, can be quickly removed by detaching it from the support structure 10. The advantage of this ability to be detached from the support structure 10 and replaced with another cover 60 is that a basic turbidity sensor can be constructed with common support structures 10, light sources 12 and photosensitive devices, 14 and 17, and be combined with many different types of covers 60. Similarly, a common cover 60 can be used with a number of different boards 100 and support structures 10. This significantly reduces the manufacturing costs of the turbidity sensor. In FIG. 6, the printed circuit board 100 and its associated components are illustrated as being detachable from the support structure 10. In the embodiment of FIG. 6, the printed circuit board 100 and its associated components are retained in position between the support structure 10 and the cover 60 without rigid attachment between the elements. However, it should be understood that alternative embodiments of the present invention could easily attach the printed circuit board 100 to the support structure 10. In this type of embodiment, the support structure 10 would comprise the lower item illustrated in FIG. 6 and the central elements, including the printed circuit board 10, the light emitting diode and the photodiodes.

Figure 7:
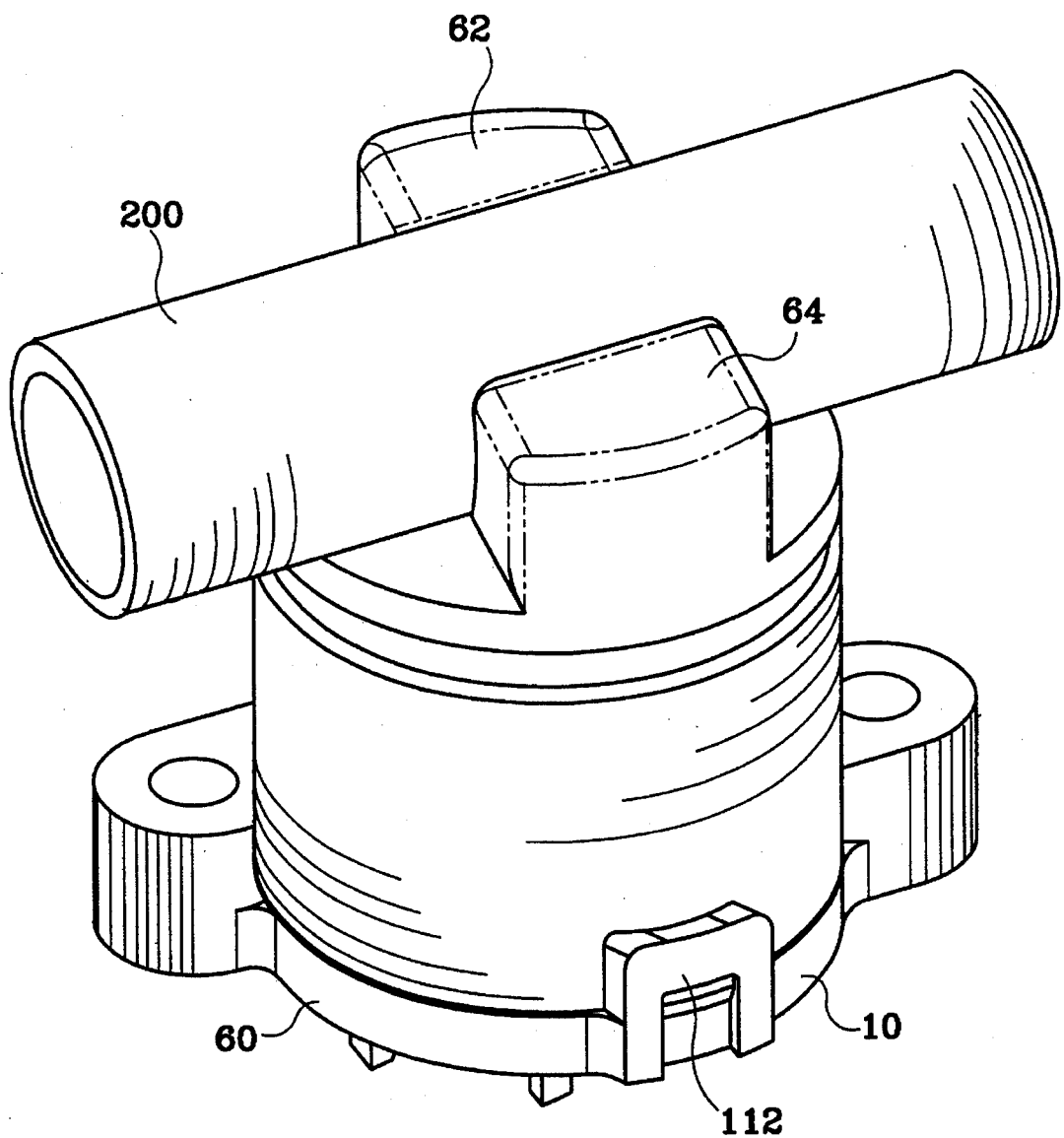
FIG. 7 is an alternative embodiment of the present invention.

FIG. 7 shows an alternative configuration of the present invention and, in conjunction with FIG. 6, illustrates the flexibility provided by the present invention. The two containments, 62 and 64, that house and protect the light source 12 and the first photosensitive device 14 are shown with a tubular structure 200 provided therebetween. The tubular structure 200 can be used when the turbidity sensor is being used in an application in which a conduit is necessary to pass the fluid through the detection zone. In comparison, the structure shown in FIG. 6 can be used when no such conduit is required. In the application shown in FIG. 6, the turbidity sensor can be disposed within a large containment of fluid and the fluid can pass in a less confined manner through the detection zone. In FIG. 7, however, the conduit 200 will restrict the passage of fluid along a predetermined path. The cover 60 shown in FIG. 7 is snapped into position to attach it to the support structure 10 in the manner described above in conjunction with FIG. 6.

Figure 8:
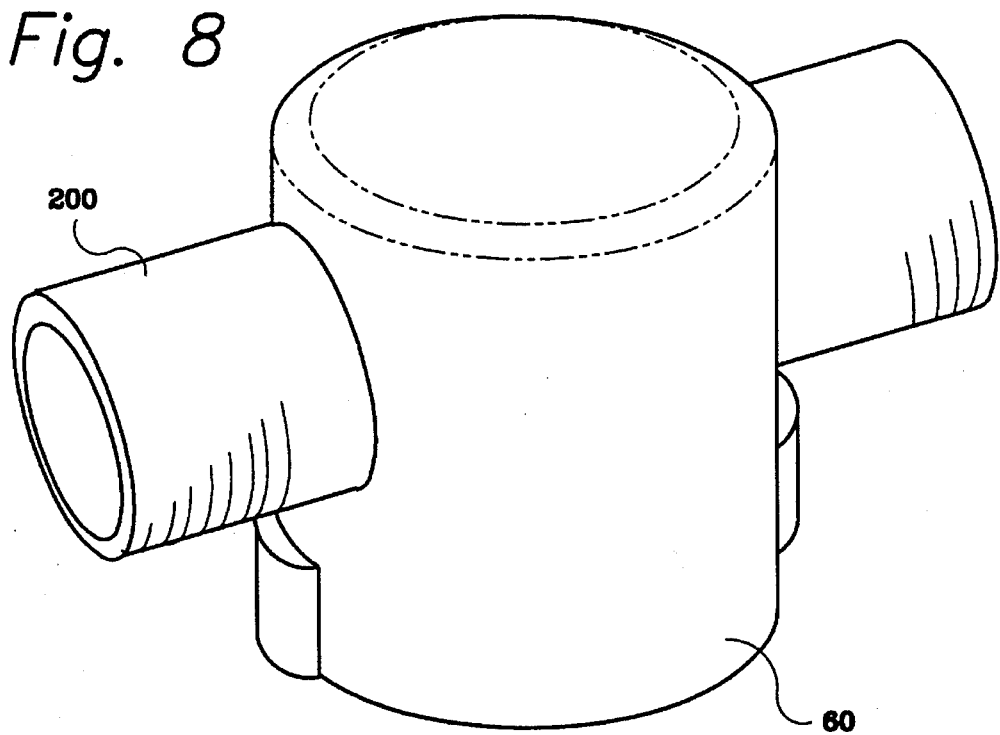
FIG. 8 is another alternative embodiment of the present invention.
Figure 9:
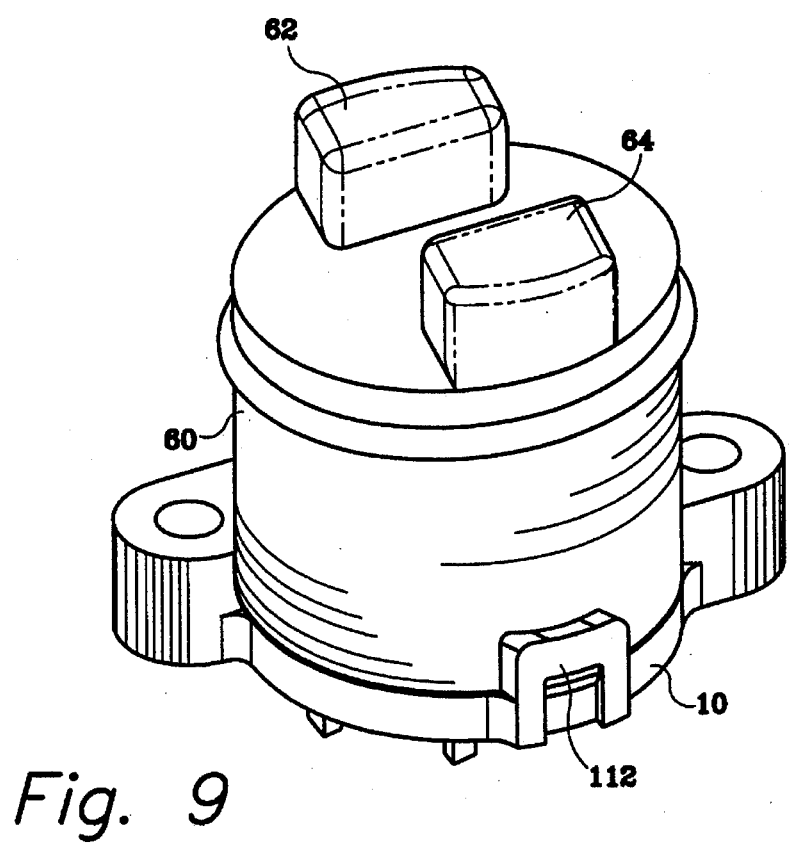
FIG. 9 is an assembled view of the embodiment shown in the exploded view of FIG. 6.

FIG. 8 shows an alternative cover 60 that has a conduit 200 formed as an integral part of the cover. The cover 60 of FIG. 8 is disposable over the cover 60 shown in FIG. 9. In the embodiment of the cover shown in FIG. 8, the individual containments, 62 and 64, shown in FIG. 7 are not separately visible but are combined into a single structure. However, it should be understood that the light source and the photosensitive devices are contained within the cover 60 and positioned to transmit light into the fluid and receive both transmitted and scattered light in the manner described above. FIGS. 8 and 9 show that the device of FIG. 9 can be quickly modified by attaching the cover of FIG. 8.

FIG. 9 shows the turbidity sensor illustrated in FIG. 6 after the cover 60 is attached to the support structure 10. The cover 60 shown in FIG. 6 can be removed in a direction that is generally perpendicular to the second plane 40 described above.

Figure 10:
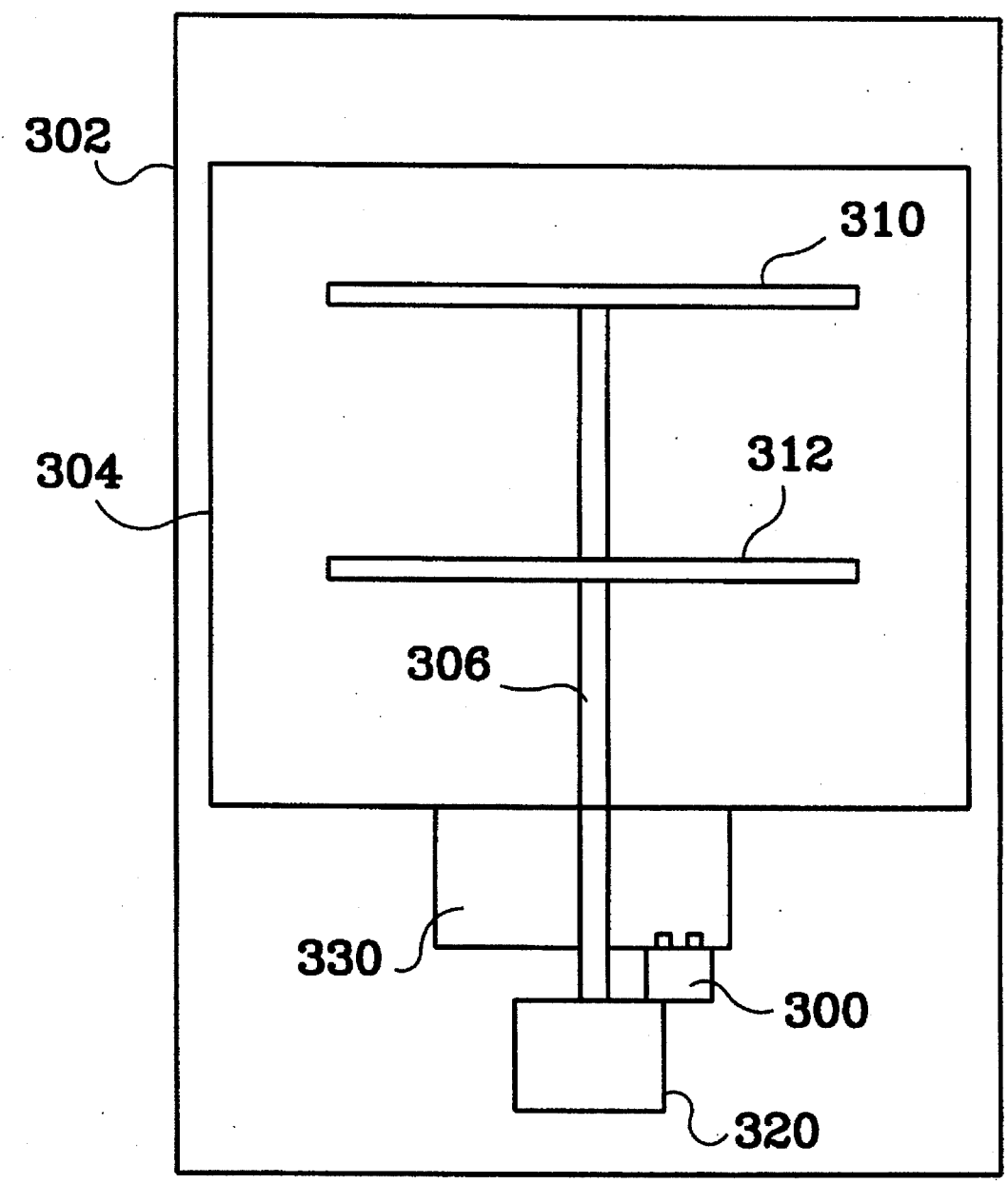
FIG. 10 shows a dishwasher with the present invention disposed therein.

FIG. 10 shows a turbidity sensor 300 used in conjunction with a dishwasher 302. As is generally known to those skilled in the art, a dishwasher 302 typically contains an inner fluid containment housing 304 in which dishes are disposed for cleansing. A vertical shaft 306 extends upward through the housing 304. The illustration in FIG. 10 shows a first wash arm 310 and a second wash arm 312 attached to the rotatable arm 306. A motor 320 is attached to the rotatable shaft 306 in order to rotate it and the wash arms, 310 and 312. A pump housing 330 is also shown in FIG. 10. In the embodiment shown schematically in FIG. 10, the turbidity sensor 300 is disposed under the pump housing 330 and extends upward through the bottom surface of the pump housing in the manner generally described above in conjunction with FIGS. 3, 4 and 5. It should be understood that FIG. 10 is highly schematic in nature and provided solely for the purpose of showing the relative positions of the turbidity sensor 300 and the pump housing 330.

Although the present invention has been described with particular specificity and illustrated to show several preferred embodiments of the present invention, it should be understood that other alternative embodiments are also within its scope.

The embodiments of the invention in which an exclusive property or right is claimed are defined as follows:

1. A turbidity sensor, comprising:

a support structure;

a light source attached to said support structure;

a photosensitive device attached to said support structure, said light source being disposed to transmit a beam of light in a direction along a first path line, said first path line being disposed within a first plane which intersects said support structure, said first path line also being disposed within a second plane which is in parallel and nonintersecting relation with a surface of said support structure, said first plane being perpendicular to said second plane, said photosensitive device being aligned to receive light from said light source which is scattered in a direction along a second path line by a fluid within a detection zone, said second path line being disposed within said first plane and being perpendicular to said second plane, said detection zone being intersected by said first and second path lines; and a cover attached to said support structure, said cover having light transmissive portions to permit light to pass through said cover along said first and second path lines.

2. The sensor of claim 1, wherein:

said cover is shaped to conduct said fluid through said detection zone.

3. The sensor of claim 1, wherein:

said cover is a portion of a pump housing.

4. The sensor of claim 1, wherein:

said sensor is disposed within a dish washer.

5. The sensor of claim 1, wherein:

said light source is a light emitting diode.

6. The sensor of claim 1, wherein:

said first photosensitive device is a photodiode.

7. The sensor of claim 1, wherein:

said cover is removable from said support structure in a direction perpendicular to said second plane.

8. A turbidity sensor, comprising:

a support structure;

a light source attached to said support structure;

a first photosensitive device attached to said support structure, said light source being aligned with said first photosensitive device to transmit a beam of light to said first photosensitive device in a direction along a first path line, said first path line being disposed within a first plane which intersects said support structure, said first path line being disposed within a second plane which is in nonintersecting relation with said support structure, said first plane being perpendicular to said second plane;

a second photosensitive device attached to said support structure and aligned to receive light from said light source which is scattered in a direction along a second path line by a fluid within a detection zone, said second path line being disposed within said first plane and being perpendicular to said second plane, said detection zone being intersected by said first and second path lines; and a cover attached to said support structure, said cover having light transmissive portions to permit light to pass through said cover along said first and second path lines, said cover being shaped to conduct said fluid through said detection zone.

9. The sensor of claim 8, wherein:

said cover is a portion of a pump housing.

10. The sensor of claim 8, wherein:

said sensor is disposed within a dish washer.

11. The sensor of claim 10, wherein:

said light source is a light emitting diode.

12. The sensor of claim 11, wherein:

said first photosensitive device is a photodiode; and said second photosensitive device is a photodiode.

13. A turbidity sensor, comprising:

a support structure;

a light source attached to said support structure, said light source being a light emitting diode;

a first photosensitive device attached to said support structure, said light source being aligned with said first photosensitive device to transmit a beam of light to said first photosensitive device in a direction along a first path line, said first path line being disposed within a first plane which intersects said support structure, said first path line being disposed within a second plane which is in nonintersecting relation with said support structure, said first plane being perpendicular to said second plane;

a second photosensitive device attached to said support structure and aligned to receive light from said light source which is scattered in a direction along a second path line by a fluid within a detection zone, said second path line being disposed within said first plane and being perpendicular to said second plane, said detection zone being intersected by said first and second path lines, said first photosensitive device being a photodiode, said second photosensitive device being a photodiode; and a cover attached to said support structure, said cover having light transmissive portions to permit light to pass through said cover along said first and second path lines, said cover being shaped to conduct said fluid through said detection zone.

14. The sensor of claim 13, wherein:

said cover is a portion of a pump housing.

15. The sensor of claim 14, wherein:

said sensor is disposed within a dish washer.

* * * * *